United States Patent [19]

Rheinheimer et al.

[11] Patent Number: 5,677,263
[45] Date of Patent: Oct. 14, 1997

[54] S-TETRAHYDROPYRANONE CYCLOHEXENONE OXIME ETHERS AND THEIR USE AS HERBICIDES

[75] Inventors: Joachim Rheinheimer, Ludwigshafen; Ulf Misslitz, Neustadt; Uwe Kardorff, Mannheim; Karl-Otto Westphalen, Speyer; Helmut Walter, Obrigheim, all of Germany

[73] Assignee: Basf Aktiengesellschaft, Ludwigshafen, Germany

[21] Appl. No.: 601,767

[22] Filed: Feb. 15, 1996

[30] Foreign Application Priority Data

Feb. 24, 1995 [DE] Germany .................. 195 06 570.0

[51] Int. Cl.⁶ .................. A01N 43/08; C07D 309/00
[52] U.S. Cl. .................. 504/292; 549/273
[58] Field of Search .................. 549/273; 504/292

[56] References Cited

U.S. PATENT DOCUMENTS

| | | | |
|---|---|---|---|
| 4,654,073 | 3/1987 | Jahn et al. | 71/88 |
| 5,022,914 | 6/1991 | Kast et al. | 71/88 |
| 5,190,573 | 3/1993 | Misslitz et al. | 504/292 |
| 5,411,936 | 5/1995 | Kast et al. | 504/244 |

FOREIGN PATENT DOCUMENTS

| | | |
|---|---|---|
| 142 741 | 5/1985 | European Pat. Off. . |
| 456 112 | 11/1991 | European Pat. Off. . |
| 38 38 309 | 5/1990 | Germany . |
| 44 15 871 | 11/1995 | Germany . |
| 93/16033 | 8/1993 | WIPO . |

*Primary Examiner*—Amelia Owens
*Attorney, Agent, or Firm*—Keil & Weinkauf

[57] ABSTRACT

5-Tetrahydropyranone cyclohexenone oxime ethers I

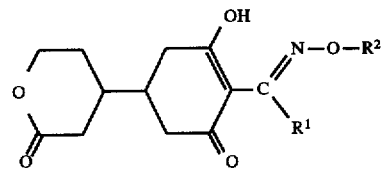

where
$R^1 = C_1-C_6$-alkyl $R^2$ = phenyl which can have attached to it 1–3 substituents; $C_1-C_4$-alkyl, $C_3-C_4$-alkenyl or $C_3-C_4$-alkynyl, each of which can be substituted by halogen, $C_1-C_3$-alkyl, unsubstituted or substituted phenyl or unsubstituted or substituted phenoxy;

and their agriculturally useful salts and esters.

8 Claims, No Drawings

5-TETRAHYDROPYRANONE CYCLOHEXENONE OXIME ETHERS AND THEIR USE AS HERBICIDES

The present invention relates to novel 5-tetrahydropyranone cyclohexenone oxime ethers of the formula I

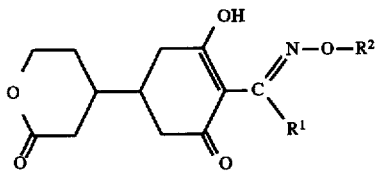

where the substituents have the following meanings:

$R^1$ is a $C_1$–$C_6$-alkyl group;

$R^2$ is the phenyl group, which can be unsubstituted or can have attached to it one to three substituents, in each case selected from the group consisting of nitro, cyano, halogen, $C_1$–$C_4$-alkyl and $C_1$–$C_4$-haloalkyl;

a $C_1$–$C_4$-alkyl, $C_3$–$C_4$-alkenyl or $C_3$–$C_4$-alkynyl group, it being possible, if desired, for these groups to have attached to them one of the following substituents: halogen, $C_1$–$C_3$-alkyl, phenyl which, if desired, can have attached to it, in turn, one to three radicals, in each case selected from the group consisting of nitro, cyano, halogen, $C_1$–$C_4$-alkyl, $C_1$–$C_4$-haloalkyl, phenyl and phenoxy, or phenoxy which, if desired, can have attached to it, in turn, one to three radicals, in each case selected from the group consisting of nitro, cyano, halogen, $C_1$–$C_4$-alkyl and $C_1$–$C_4$-haloalkyl;

and the agriculturally useful salts of I and the esters of I with $C_1$–$C_{10}$-carboxylic acids or inorganic acids.

Furthermore, the invention relates to the use of these compounds as herbicides, to herbicidal compositions comprising these compounds as active ingredients, to processes for the preparation of these herbicidal compositions, and to methods of controlling undesirable vegetation using the compounds I.

There have already been disclosed in the literature herbicidally active cyclohexanediones of the formula I'

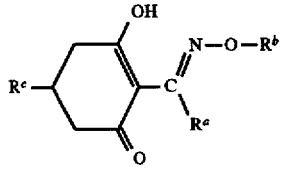

where $R^a$, $R^b$ and $R^c$ have, inter alia, the following meanings:

EP-A 142 741 ($R^a$=$C_1$–$C_4$-alkyl; $R^b$=$C_1$–$C_4$-alkyl, $C_3$–$C_4$-alkenyl, which can have attached to it 1–3 halogen atoms, propargyl; $R^c$=tetrahydropyran-4-yl);

DE-A 38 38 309 ($R^a$=$C_1$–$C_6$-alkyl; $R^b$=substituted 4-phenylbutylene or 4-phenylbutenylene radical; $R^c$=substituted 5- to 7-membered heterocycle);

EP-A 456 112 ($R^a$=$C_1$–$C_6$-alkyl; $R^b$=substituted 3-phenoxypropylene or 2-phenoxyethylene radical; $R^c$=substituted 5- to 7-membered heterocycle).

Since the herbicidal properties of the known compounds are not always entirely satisfactory, in particular with regard to their selectivity against grass weeds in Gramineae crops, it was an object of the invention to provide novel cyclohexenone oxime ethers with which better targeted control of grass weeds in Gramineae crops such as rice and maize can be achieved than hitherto possible.

Accordingly, we have found the 5-tetrahydropyranone cyclohexenone oxime ethers I defined at the outset. We have furthermore found their use as herbicides, herbicidal compositions which comprise the compounds I, a process for the preparation of these compositions, and a method of controlling undesirable vegetation using the compounds I.

The 5-tetrahydropyranone cyclohexenone oxime ethers I can be obtained by various routes, preferably in a manner known per se from known cyclohexenones of the formula II which have been disclosed in accordance with the following equation:

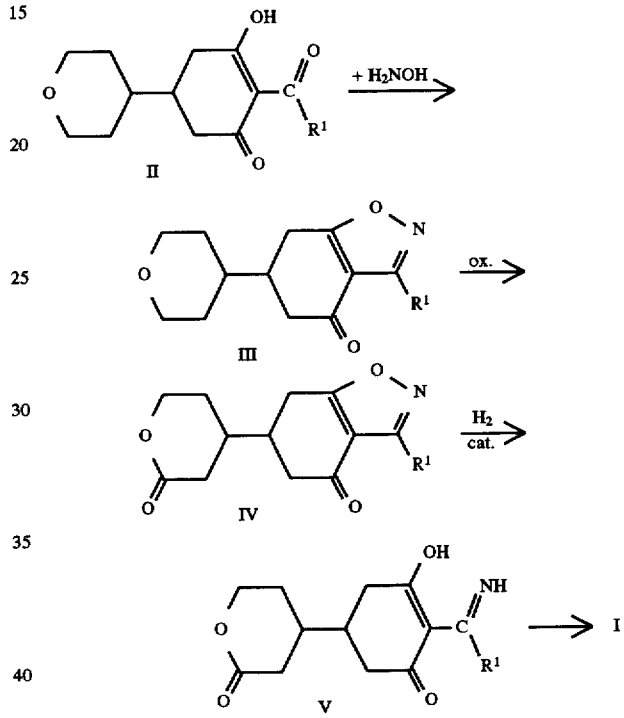

II is preferably reacted with a suitable hydroxylamine salt, in particular its hydrochloride. A solvent which has proved particularly expedient for this purpose is water.

The reaction is carried out in the presence of a base, an amount of approximately 0.5 to 2 mol equivalent of base, based on the ammonium compound, generally being sufficient.

Examples of suitable bases are carbonates, hydrogen carbonates, acetates, alcoholates or oxides of alkali metals or alkaline earth metals, in particular sodium hydroxide, potassium hydroxide, magnesium oxide or calcium oxide. Organic bases, such as pyridine, and tert-amines, such as triethylamine, are furthermore suitable.

A variant of the process consists in reacting II with the free hydroxylamine base $H_2NOH$, for example in the form of an aqueous solution, in the absence of a base; depending on the solvent used, a one- or two-phase reaction mixture is obtained.

Examples of suitable solvents for this variant are alcohols, such as methanol, ethanol, isopropanol and cyclohexanol, aliphatic and aromatic, unchlorinated or chlorinated hydrocarbons, such as hexane, cyclohexane, methylene chloride, toluene and dichloroethane, esters, such as ethyl acetate, nitriles, such as acetonitrile, and cyclic ethers, such as dioxane and tetrahydrofuran.

The cyclohexenone II and the hydroxylamine, or its salt, are expediently employed in approximately stoichiometric amounts, but an excess of one or the other component of up to approximately 100 mol % may also be advantageous.

The reaction temperature is generally from 0° C. to the boiling point of the reaction mixture, preferably from 20° to 80° C.

A suitable oxidant for the oxidation of III to the lactone IV is, for example, chromium trioxide. The oxidation is generally successfully carried out at from 0° C. to the boiling point of the reaction mixture.

A particularly suitable solvent is acetic anhydride, but halogenated hydrocarbons, such as methylene chloride, are also suitable examples.

[Laboratory Practical in Organic Chemistry], VEB Deutscher Verlag der Wissenschaften, 17th edition, Berlin 1988, pp. 405–408).

Depending on the meaning of $R^2$ and the position of the pyranone ring on the cyclohexanone skeleton, the 5-tetrahydropyranone cyclohexenone oxime ethers I can be obtained, from their preparation, as an isomer mixture, with E/Z isomer mixtures and also R/S enantiomer or diastereoisomer mixtures being possible. If desired, the isomer mixtures can be separated by customary methods, for example by chromatography or by crystallization.

The 5-tetrahydropyranone cyclohexenone oxime ethers I can be written as several tautomeric formulae, all of which are embraced by the invention:

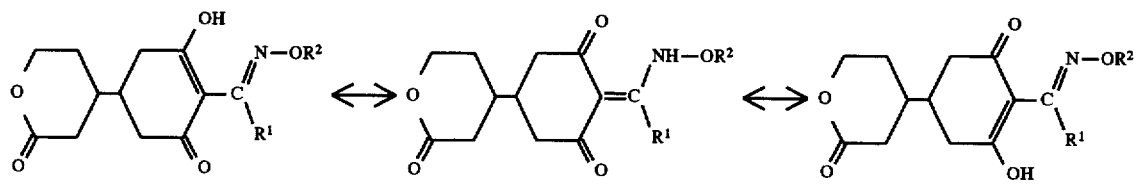

The oxidant is generally employed in at least equimolar amounts based on III. However, in general, a large excess of oxidant has proved to be particularly advantageous.

IV is generally hydrogenated in a solvent or diluent which is customary for such reactions, for example in an alcohol, such as methanol, ethanol, n-propanol and isopropanol, in an ether, such as diethyl ether and tetrahydrofuran, or in an ester, such as ethyl acetate. Mixtures of these are also suitable.

A particularly suitable hydrogenating agent is molecular hydrogen in the presence of a suitable noble-metal catalyst, such as palladium (on charcoal) or platinum.

As a rule, the hydrogen is used in excess, and the process is carried out at a pressure of approximately 1 to 200 bar, preferably 1 to 50 bar.

The reaction temperature is generally at from (−78) to approximately 130° C., preferably from 0° to 100° C.

V can be converted to I by methods similar to other reactions of this type which are described in EP-A 368 227, EP-A 456 112, U.S. Pat. No. 4,249,937 and WO 92/08696.

Unless otherwise specified, the reaction steps described above are expediently carried out under atmospheric pressure or under the inherent pressure of the diluent in question.

The 5-tetrahydropyranone cyclohexenone oxime ethers I according to the invention can be present in the form of their agriculturally useful salts or as enol esters, the nature of the salt or ester generally not being critical. As a rule, bases suitable for salt formation and acids suitable for esterification are those which do not adversely affect the herbicidal action of I.

Alkali metal salts of the compounds I can be obtained by treating the 3-hydroxycyclohexenone compounds with sodium hydroxide, sodium alcoholate, potassium hydroxide or potassium alcoholate in aqueous solution or in an organic solvent, such as methanol, ethanol, acetone and toluene.

Other metal salts, such as manganese, copper, zinc, iron, calcium, magnesium and barium salts can be prepared from the sodium salts in the customary manner, and ammonium and phosphonium, sulfonium and sulfoxonium salts by means of ammonium, phosphonium, sulfonium or sulfoxonium hydroxides.

The esters of the compounds I can also be obtained in the customary manner (cf., for example, Organikum The collective terms halogen, alkyl, haloalkyl, alkenyl and alkynyl which are used in the definitions of the substituents are short for an individual innumeration of the individual members of these groups. All alkyl, haloalkyl, alkenyl and alkynyl moieties can be straight-chain or branched. The haloalkyl moieties can have attached to them identical or different halogen atoms.

Individual meanings are, for example, halogen: fluorine, chlorine, bromine, iodine;

$C_1$–$C_4$-alkyl (group): methyl, ethyl, n-propyl, 1-methylethyl, n-butyl, 1-methylpropyl, 2-methylpropyl, 1,1-dimethylethyl;

$C_1$–$C_3$-alkyl: methyl, ethyl, n-propyl, 1-methylethyl;

$C_1$–$C_4$-haloalkyl: $C_1$–$C_4$-alkyl as mentioned above which is partially or fully substituted by fluorine, chlorine and/or bromine, e.g. chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl;

$C_3$–$C_4$-alkenyl group: 1-propenyl, 2-propenyl, 1-methylethenyl, 5 1-butenyl, 2-butenyl, 3-butenyl, 1-methyl-1-propenyl, 1-methyl-2-propenyl, 2-methyl-1-propenyl, 2-methyl-2-propenyl;

$C_3$–$C_4$-alkynyl group: prop-1-yn-1-yl, prop-2-yn-3-yl, n-but-1-yn-1-yl, n-but-1-yn-4-yl, n-but-2-yn-1-yl.

With a view to the herbicidal activity of the 5-tetrahydropyranone cyclohexenone oxime ethers I, the following meanings of the substituents are particularly preferred, both alone and in combination:

$R^1$ is ethyl and propyl;

$R^2$ is the phenyl group, unsubstituted or mono- to trisubstituted by nitro, cyano;

halogen, in particular fluorine, chlorine;

$C_1$–$C_4$-alkyl, in particular methyl;

$C_1$–$C_4$-haloalkyl, in particular trifluoromethyl;

a $C_1$–$C_4$-alkyl, $C_3$–$C_4$-alkenyl or $C_3$–$C_4$-alkynyl group, it being possible for these groups, if desired, to have attached to them one of the following substituents:

halogen, in particular fluorine, chlorine;

$C_1$–$C_3$-alkyl, in particular methyl;

phenyl which can be unsubstituted or can have attached to it one to three substituents selected from the group consisting of nitro, cyano;

halogen, in particular fluorine, chlorine;

$C_1$–$C_4$-alkyl, in particular methyl;

$C_1$–$C_4$-haloalkyl, in particular trifluoromethyl;

phenyl, phenoxy;

phenoxy which can be unsubstituted or can have attached to it one to three substituents selected from the group consisting of nitro, cyano;

halogen, in particular fluorine, chlorine;

$C_1$–$C_4$-alkyl, in particular methyl;

$C_1$–$C_4$-haloalkyl, in particular trifluoromethyl; very particularly preferred are ethyl, chloroallyl, 2-phenoxypropyl, 3-phenylpropenyl and 4-phenylbutenyl, it being possible for the phenyl rings to be unsubstituted or to have attached to them one to three chlorine and/or fluorine atoms.

Suitable salts of the 5-tetrahydropyranone cyclohexenone oxime ethers of the formula I are agriculturally useful salts, for example alkali metal salts, in particular the sodium or potassium salt, alkaline earth metal salts, in particular the calcium, magnesium or barium salt, manganese, copper, zinc or iron salt, and ammonium, phosphonium, sulfonium or sulfoxonium salts, for example ammonium salts, tetraalkylammonium salts, benzyltrialkylammonium salts, trialkylsulfonium salts or trialkylsulfoxonium salts.

Agriculturally useful esters are preferably to be understood as meaning the esters of $C_1$–$C_{10}$-fatty acids, in particular $C_1$–$C_6$-alkylcarboxylic acids, such as methylcarboxylic acid (acetic acid), ethylcarboxylic acid (propionic acid), propylcarboxylic acid (butyric acid), 1-methylethylcarboxylic acid (isobutyric acid), butylcarboxylic acid, 1-methylpropylcarboxylic acid, 2-methylpropylcarboxylic acid, 1,1-dimethylethylcarboxylic acid, pentylcarboxylic acid, 1-methylbutylcarboxylic acid, 2-methylbutylcarboxylic acid, 3-methylbutylcarboxylic acid, 1,1-dimethylpropylcarboxylic acid, 1,2-dimethylpropylcarboxylic acid, 2,2-dimethylpropylcarboxylic acid, 1-ethylpropylcarboxylic acid, benzoic acid and halogen-substituted benzoic acids, hexylcarboxylic acid, 1-methylpentylcarboxylic acid, 2-methylpentylcarboxylic acid, 3-methylpentylcarboxylic acid, 4-methylpentylcarboxylic acid, 1,1-dimethylbutylcarboxylic acid, 1,2-dimethylbutylcarboxylic acid, 1,3-dimethylbutylcarboxylic acid, 2,2-dimethylbutylcarboxylic acid, 2,3-dimethylbutylcarboxylic acid, 3,3-dimethyl-butylcarboxylic acid, 1-ethylbutylcarboxylic acid, 2-ethylbutylcarboxylic acid, 1,1,2-trimethylpropylcarboxylic acid, 1,2,2-trimethylpropylcarboxylic acid, 1-ethyl-1-methylpropylcarboxylic acid and 1-ethyl-2-methylpropylcarboxylic acid.

The 5-tetrahydropyranone cyclohexenone oxime ethers I, their salts and esters—in the form of the isomer mixtures and also the pure isomers—are suitable as herbicides. In general, they are tolerated by, and thus selective in, broad-leaved crops and in monocotyledon (monocot) species which do not belong to the Gramineae. Some of the compounds I according to the invention are also suitable for the selective control of undesirable grasses in Gramineae crops.

This effect is mainly pronounced at low application rates.

In addition, the compounds I can also be used in crops which, as a result of breeding, including genetic engineering methods, tolerate the action of herbicides.

The 5-tetrahydropyranone cyclohexenone oxime ethers I, or the herbicidal compositions comprising them, can be applied, for example, in the form of ready-to-spray aqueous solutions, powders, suspensions, also highly concentrated aqueous, oily or other suspensions or dispersions, emulsions, oil dispersions, pastes, dusts, materials for spreading or granules by means of spraying, atomizing, dusting, spreading or pouring. The use forms depend on the intended purposes; in any case, they should guarantee the finest possible distribution of the active ingredients according to the invention.

The compounds I are generally suitable for the preparation of ready-to-spray solutions, emulsions, pastes or oil dispersions. Suitable additives are mineral oil fractions of medium to high boiling point, such as kerosine or diesel oil, furthermore coaltar oils and oils of vegetable or animal origin, aliphatic, cyclic and aromatic hydrocarbons, e.g. paraffin, tetrahydronaphthalene, alkylated naphthalenes or their derivatives, alkylated benzenes or their derivatives, methanol, ethanol, propanol, butanol, cyclohexanol, cyclohexanone or strongly polar solvents, such as N-methylpyrrolidone or water.

Aqueous use forms can be prepared from emulsion concentrates, suspensions, pastes, wettable powders or water-dispersible granules by adding water. To prepare emulsions, pastes or oil dispersions, the substances, either as such or dissolved in an oil or solvent, can be homogenized in water by means of a wetting agent, tackifier, dispersant or emulsifier. Alternatively, it is also possible to prepare concentrates comprising active ingredient, wetting agent, tackifier, dispersant or emulsifier and, if desired, solvent or oil, and these concentrates are suitable for dilution with water.

Suitable surfactants (adjuvants) are the alkali metal salts, alkaline earth metal salts and ammonium salts of aromatic sulfonic acids, e.g. ligno-, phenol-, naphthalene and dibutylnaphthalenesulfonic acid, or of fatty acids, alkyl- and alkylarylsulfonates, alkyl, lauryl ether and fatty alcohol sulfates, and salts of sulfated hexa-, hepta- and octadecanols, and also of fatty alcohol glycol ethers, condensates of sulfonated naphthalene or its derivatives with formaldehyde, condensates of naphthalene, or of the naphthalenesulfonic acids, with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, or polyoxypropylene alkyl ethers, lauryl alcohol polyglycol ether acetate, sorbitol esters, lignosulfite waste liquors or methylcellulose.

Powders, materials for spreading and dusts can be prepared by mixing or grinding the active ingredients together with a solid carrier.

Granules, e.g. coated granules, impregnated granules and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas, and products of vegetable origin, such as cereal meal, tree bark meal, wood meal and nutshell meal, cellulose powder or other solid carriers.

The concentrations of the active ingredients I in the ready-to-use preparations can be varied within wide ranges. The formulations generally comprise from 0.001 to 98% by weight, preferably from 0.01 to 95% by weight, of at least one active ingredient. The active ingredients are employed in a purity from 90% to 100%, preferably 95% to 100% (in accordance with NMR spectrum).

The compounds I according to the invention can be formulated for example as follows:

I. 20 parts by weight of the compound No. 2 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100000 parts by weight of water and finely distributing it therein gives an aqueous dispersion comprising 0.02% by weight of the active ingredient.

II. 20 parts by weight of the compound No. 4 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100000 parts by weight of water and finely distributing it therein gives an aqueous dispersion comprising 0.02% by weight of the active ingredient.

III. 20 parts by weight of the active ingredient No. 8 are dissolved in a mixture composed of 20 parts by weight of cyclohexanone, 65 parts by weight of a mineral oil fraction of boiling point 210° to 280° C. and 10 parts by weight of the adduct of 40 mol of ethylene oxide to 1 mol of castor oil. Pouring the solution into 100000 parts by weight of water and finely distributing it therein gives an aqueous dispersion comprising 0.02% by weight of the active ingredient.

IV. 20 parts by weight of the active ingredient No. 10 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20000 parts by weight of water gives a spray mixture comprising 0.1% by weight of the active ingredient.

V. 3 parts by weight of the active ingredient No. 19 are mixed with 97 parts by weight of finely divided kaolin. This gives a dust comprising 3% by weight of the active ingredient.

VI. 20 parts by weight of the active ingredient No. 26 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. 12 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound No. 24 is dissolved in a mixture composed of 80 parts by weight of cyclohexanone and 20 parts by weight of Emulphor El[1]). This gives a stable emulsion concentrate.

[1]) ethoxylated castor oil

Application of the herbicidal compositions, or of the active ingredients, can be effected pre- or post-emergence. If the active ingredients are less well tolerated by certain crop plants, application techniques may be used where the herbicidal compositions are sprayed, with the aid of the spraying equipment, in such a way that the active ingredients come into as little contact as possible with the leaves of the sensitive crop plants while reaching the leaves of undesirable plants which grow thereunder, or the naked soil surface (post-directed, lay-by).

Depending on the purpose of the control, the season, the target plants and the growth stage, the application rates of active ingredient are from 0.001 to 3.0, preferably 0.01 to 1.0, kg of at least one active ingredient (a.i.) of the formula I per ha.

With a view to the versatility of the application methods, the 5-tetrahydropyranone cyclohexenone oxime ethers I, or compositions comprising them, can additionally be employed in a further number of crop plants for eliminating undesirable plants. Suitable crops are, for example, the following:

*Allium cepa, Ananas comosus, Arachis hypogaea, Asparagus officinalis, Beta vulgaris* ssp. *altissima, Beta vulgaris* ssp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea bataras, Juglans regia, Lens culinaris, Linum usitatissimum, Lycopersicon lycopersicum,* Malus spp., *Manihot esculenta, Medicago sativa,* Musa spp., *Nicotiana tabacum* (*N.rustica*), *Olea europaea, Oryza sativa, Phaseolus lunatus, Phaseolus vulgaris, Picea abies,* Pinus spp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera, Zea mays.*

To widen the spectrum of action and to achieve synergistic effects, the 5-tetrahydropyranone cyclohexenone oxime ethers I may be mixed with a large number of representatives of other groups of herbicidal or growth-regulating active ingredients and then applied concomitantly. Suitable components for mixtures are 1,2,4-thiadiazoles, 1,3,4-thiadiazoles, amides, aminophosphoric acid and its derivatives, aminotriazoles, anilides, aryloxyheteroaryloxyalkanoic acids and their derivatives, benzoic acid and its derivatives, benzothiazinones, 2-(hetaroyl/aroyl)-1,3-cyclohexanediones, heteroaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofuranes, dihydrofuran-3-ones, dinitroanilines, dinitrophenols, diphenyl ethers, dipyridyls, halocarboxylic acids and their derivatives, ureas, 3-phenyluralics, imidazoles, imidazolinones, N-phenyl-3,4,5,6-tetrahydrophthalimide, oxadiazoles, oxiranes, phenols, aryloxy- and heteroaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamide and uracils.

It may furthermore be advantageous to apply the compounds I, alone or in combination with other herbicides, together with further crop protection agents, for example with pesticides or agents for controlling phytopathogenic fungi or bacteria. Also of interest is the miscibility with mineral salt solutions, which are employed for treating nutrient and trace element deficiencies. Non-phytotoxic oils and oil concentrates may also be added.

Preparation example

2-{1-(2-[4-Chlorophenoxy)propoxy]iminopropyl)-3-hydroxy-5-(tetrahydropyran-2-on-4-yl)-2-cyclohexen-1-one (Compound No. 1)

a) 3-Ethyl-6-(tetrahydropyran-4-yl)-6,7-dihydro-5H-benzo[d]isoxazol-4-one:

A solution of 113.4 g (0.44 mol) of 3-hydroxy-2-propionyl-5-(tetrahydropyran-4-yl)-2-cyclohexen-1-one in 1 l of ethanol was added dropwise to 34.8 g (0.5 mol) of hydroxylamine hydrochloride, 41.0 g (0.5 mol) of sodium acetate and 10 ml of 50% by weight strength sodium hydroxide solution in 500 ml of water. The reaction mixture was subsequently heated at 80° C. and stirred for 2 hours at this temperature. The mixture was then allowed to cool to approximately 20° C. The product was extracted 3 times using methyl tert-butyl ether and, after the ether phase had been dried over sodium sulfate, isolated by removing the ether under reduced pressure. The crude product was purified chromatographically on silica gel 60 (eluent: methyl tert-butyl ether/ethyl acetate). Yield 65 g.

b) 3-Ethyl-6-(tetrahydropyran-2-on-4-yl )-6,7-dihydro-5H-benzo[d]isoxazol-4-one:

12 g (0.12 mol) of chromium trioxide were added to 30 g (0.12 mol) of 3-ethyl-6-(tetrahydropyran-4-yl)-6,7-dihydro-5H-benzo[d]isoxazol-4-one in 300 ml of acetic anhydride, during which process the temperature of the mixture rose to 70° C. A further two portions of in each case 6 g (0.06 mol) of chromium trioxide were added at 1-hour intervals, whereupon the reaction mixture was stirred at approximately 20° C. for a further 4 hours. The mixture was subsequently stirred into 1 l of ice-water. The product was then extracted using ethyl acetate. The organic phase was washed with water and a concentrated sodium chloride solution, dried over sodium sulfate and finally concentrated. The crude product was purified chromatographically on silica gel 60 (eluent: methyl tert-butyl ether/ethyl acetate). Yield: 22 g.

c) 3-Hydroxy-2-(1-iminopropyl)-5-(tetrahydropyran-2-on-4-yl)-2-cyclohexen-1-one:

20 g (0.08 mol) of 3-ethyl-6-(tetrahydropyran-2-on-4-yl)-6,7-dihydro-5H-benzo[d]isoxazol-4-one, 6.4 g (0.06 mol) of triethylamine and 1.6 g of palladium on active carbon (10%) in 100 ml of ethanol were treated at 40° C. for 24 hours with hydrogen under a pressure of 5 bar. Undissolved components were subsequently removed by filtration, whereupon the filtrate was concentrated under reduced pressure. The residue was purified chromatographically on silica gel 60 (eluent: methyl tert-butyl ether/ isopropanol). Yield: 15 g.

d) Desired product:

A mixture of 7.0 g (0.02 mol) of 3-hydroxy-2-(1-iminopropyl)-5-(tetrahydropyran-2-on-4-yl)-2-cyclohexen-1-one, 3.7 g (0.02 mol) of o-(2-(4-chlorophenoxy)propyl)hydroxylamine and 100 ml of methanol was stirred for 5 hours at approximately 20° C., whereupon the reaction mixture was concentrated under reduced pressure. The crude product was purified chromatographically on silica gel 60 (eluent: methyl tert-butyl ether/ethyl acetate). Yield: 2.2 g (oil, $^1$H NMR see Table 1).

Other 5-tetrahydropyranone cyclohexenone oxime ethers I which were prepared, or can be prepared, by similar methods are listed in Table 1 below:

TABLE 1

I

| No. | $R^1$ | $R^2$ | 1H NMR (in CDCl$_3$): δ [ppm] (selected signals) |
|---|---|---|---|
| 1 | ethyl | 2-(4-chlorophenoxy)propyl | 1.09 (t); 1.35 (d); 4.43 (m); 4.64 (m); 6.86 (d); 7.20 (d) |
| 2 | ethyl | E-3-chloro-2-propenyl | 1.12 (t); 4.52 (d); 5.97–6.40 (m) |
| 3 | ethyl | (3-chlorophenyl)methyl | |
| 4 | ethyl | (4-phenylphenyl)methyl | 4.50 (m); 5.17 (m); 7.30–7.70 (m) |
| 5 | ethyl | (3-phenoxyphenyl)methyl | |
| 6 | propyl | 2-(4-chlorophenoxy)propyl | |
| 7 | propyl | E-3-chloro-2-propenyl | |
| 8 | ethyl | ethyl | 1.15 (t); 1.32 (t); 2.92 (q); 4.12 (q); 4.47 (m) |
| 9 | ethyl | 2-(2,4-difluorophenoxy)propyl | 1.10 (t); 1.35 (d); 4.50 (m); 6.70–7.10 (m) |
| 10 | ethyl | 2-(4-fluorophenoxy)propyl | 1.10 (t); 1.35 (d); 4.50 (m); 6.90 (m) |
| 11 | ethyl | 2-(3,5-dichlorophenoxy)propyl | 1.09 (t); 1.38 (d); 4.66 (m); 6.85 (s); 6.93 (s) |
| 12 | ethyl | 2-(2,4-dichlorophenoxy)propyl | 1.10 (t); 1.39 (d); 4.63 (m); 6.90 (d); 7.17 (dd); 7.35 (d) |
| 13 | ethyl | 2-(4-fluorophenoxy)propyl | |
| 14 | ethyl | 2-(4-fluorophenoxy)propyl | |
| 15 | ethyl | 2-(4-fluorophehoxy)propyl | |
| 16 | ethyl | 2-(4-fluorophenoxy)propyl | |
| 17 | ethyl | 4-(4-fluorophenyl)-2-butenyl | |
| 18 | ethyl | 4-(4-chlorophenyl)-2-butenyl | |
| 19 | ethyl | 2-propenyl | 1.25 (t); 4.63 (d); 5.37 (m); 6.03 (m) |
| 20 | ethyl | E-2-butenyl | |

TABLE 1-continued

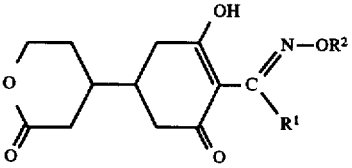

| No. | R¹ | R² | 1H NMR (in CDCl₃): δ [ppm] (selected signals) |
|---|---|---|---|
| 21 | ethyl | 2-(4-fluorophenoxy)ethyl | |
| 22 | ethyl | 2-(4-chlorophenoxy)ethyl | |
| 23 | ethyl | 3-(4-fluorophenoxy)propyl | |
| 24 | ethyl | 3-(4-chlorophenoxy)propyl | 1.13 (t); 4.27 (m); 4.45 (m); 6.83 (d); 7.23 (d) |
| 25 | ethyl | 2-(4-fluorophenoxy)propyl | |
| 26 | ethyl | 3-(2,4-difluorophenoxy)propyl | 1.13 (t); 4.27 (m); 4.45 (m); 6.73-7.05 (m). |
| 27 | ethyl | 3-(2,4-dichlorophenoxy)propyl | 1.12 (t); 4.27 (m); 4.45 (m); 6.83 (d); 7.15 (dd); 7.37 (d) |
| 28 | propyl | ethyl | |
| 29 | propyl | 2-(2,4-difluorophenoxy)propyl | |
| 30 | propyl | 2-(4-fluorophenoxy)propyl | |
| 31 | propyl | 2-(3,5-dichlorophenoxy)propyl | |
| 32 | propyl | 2-(2,4-dichlorophenoxy)propyl | |
| 33 | propyl | 2-(4-fluorophenoxy)propyl | |
| 34 | propyl | 2-(4-fluorophenoxy)propyl | |
| 35 | propyl | 2-(4-fluorophenoxy)propyl | |
| 36 | propyl | 2-(4-fluorophenoxy)propyl | |
| 37 | propyl | 4-(4-fluorophenyl)-2-butenyl | |
| 38 | propyl | 4-(4-chlorophenyl)-2-butenyl | |
| 39 | propyl | 2-propenyl | |
| 40 | propyl | E-2-butenyl | |
| 41 | propyl | 2-(4-fluorophenoxy)ethyl | |
| 42 | propyl | 2-(4-chlorophenoxy)ethyl | |
| 43 | propyl | 3-(4-fluorophenoxy)propyl | |
| 44 | propyl | 3-(4-chlorophenoxy)propyl | |
| 45 | propyl | 2-(4-fluorophenoxy)propyl | |
| 46 | propyl | 3-(2,4-difluorophenoxy)propyl | |
| 47 | propyl | 3-(2,4-dichlorophenoxy)propyl | |
| 48 | propyl | 4-(4-fluorophenyl)-3-butenyl | |
| 49 | ethyl | 4-(4-fluorophenyl)-3-butenyl | |
| 50 | propyl | 4-(4-chlorophenyl)-3-butenyl | |
| 51 | ethyl | 4-(4-chlorophenyl)-3-butenyl | |
| 52 | propyl | 4-(2,4-difluorophenyl)-3-butenyl | |
| 53 | ethyl | 4-(2,4-difluorophenyl)-3-butenyl | |
| 54 | propyl | 4-(2,4-dichlorophenyl)-3-butenyl | |
| 55 | ethyl | 4-(2,4-dichlorophenyl)-3-butenyl | |

Use examples

The herbicidal action of the 5-tetrahydropyranone cyclohexenone oxime ethers of the formula I was demonstrated by greenhouse experiments:

The culture containers used were plastic flowerpots containing loamy sand with approximately 3.0% of humus as the substrate. The seeds of the test plants were sown separately for each species.

In the case of the pre-emergence treatment, the active ingredients, which were suspended or emulsified in water, were applied directly after sowing by means of finely distributing nozzles. The containers were irrigated gently to promote germination and growth and subsequently covered with translucent plastic hoods until the plants had rooted. This cover resulted in uniform germination of the test plants, unless germination was adversely affected by the active ingredients.

For the post-emergence treatment, the test plants were first grown to a plant height of 3 to 15 cm, depending on the growth form, and only then treated with the active ingredients which were suspended or emulsified in water. For this purpose, the test plants were either sown directly and grown in the same containers, or first grown separately as seedlings and transplanted to the test containers a few days prior to treatment.

The application rate for the post-emergence treatment was 0.25 and 0.125 kg of active ingredient (a.i.) per ha.

The plants were kept at 10°–25° C. or 20°–35° C., depending on the species. The test period extended to 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage or normal course of growth.

The plants used in the greenhouse experiments belonged to the following species:

| Scientific name | Common name |
|---|---|
| Digitaria sanguinalis | crabgrass |
| Setaria faberii | giant foxtail |
| Setaria italica | foxtail millet |
| Setaria viridis | green foxtail |
| Triticum aestivum | winter wheat |

The result showed that the compounds No. 2 and 26 are capable of effecting very good control of undesirable grasses in wheat as exemplary crops. The comparison compound A

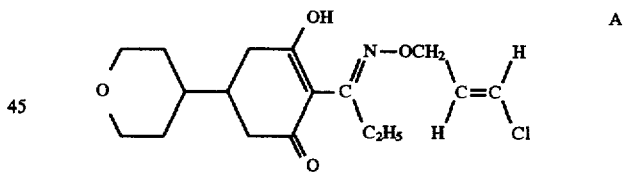

which is disclosed in EP-A 142 741, and the comparison compound B,

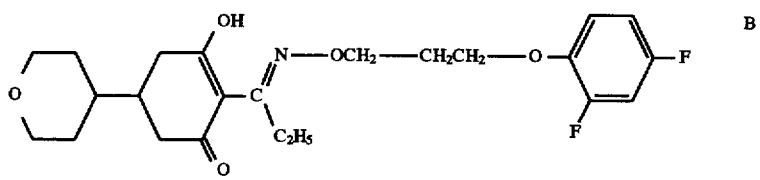

which is disclosed in WO 93/16033, in contrast, damaged the grass weeds and also the crop plant.

We claim:

1. A 5-tetrahydropyranone cyclohexenone oxime ether of the formula I

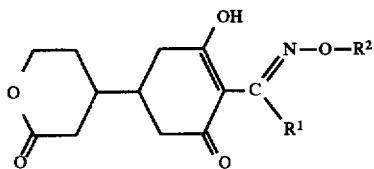

where the substituents have the following meanings:

$R^1$ is a $C_1$–$C_6$-alkyl group;

$R^2$ is a phenyl group, which can be unsubstituted or can have attached to it one to three substituents selected from the group consisting of nitro, cyano, halogen, $C_1$–$C_4$-alkyl and $C_1$–$C_4$-haloalkyl;

a $C_1$–$C_4$-alkyl, $C_3$–$C_4$-alkenyl or $C_3$–$C_4$-alkynyl group, it being possible for these groups to have attached to them one of the following substituents:

halogen, $C_1$–$C_3$-alkyl, phenyl which, can have attached to it one to three radicals selected from the group consisting of nitro, cyano, halogen, $C_1$–$C_4$-alkyl, $C_1$–$C_4$-haloalkyl, phenyl and phenoxy, or phenoxy which can have attached to it, one to three radicals, selected from the group consisting of nitro, cyano, halogen, $C_1$–$C_4$-alkyl and $C_1$–$C_4$-haloalkyl;

and the agriculturally useful salts of I and the esters of I with $C_1$–$C_{10}$-carboxylic acids or inorganic acids.

2. A herbicidal composition comprising a herbicidally active amount of at least one 5-tetrahydropyranone cyclohexenone oxime ether of the formula I and/or of an agriculturally useful salt of I and/or an ester of I with an acid, as defined in claim 1, and at least one inert liquid and/or solid carrier.

3. A method of controlling undesirable vegetation, which comprises allowing to act a herbicidally active amount of at least one 5-tetrahydropyranone cyclohexenone oxime ether of the formula I and/or of an agriculturally useful salt of I and/or an ester of I with an acid, as claimed in claim 1, on plants, their environment or seed.

4. A 5-tetrahydropyranone cyclohexenone oxime ether of the formula I as defined in claim 1, wherein $R^1$ is ethyl or propyl.

5. A 5-tetrahydropyranone cyclohexenone oxime ether of the formula I as defined in claim 1, wherein $R^1$ is ethyl or propyl and $R^2$ is selected from the group consisting of 2-(4-chlorophenoxy)propyl, E-3-chloro-2-propenyl, (3-chlorophenyl)methyl, (4-phenylphenyl)methyl, (3-phenoxyphenyl)methyl, and ethyl.

6. A 5-tetrahydropyranone cyclohexenone oxime ether of the formula I as defined in claim 1, wherein $R^1$ is ethyl and $R^2$ is E-3-chloro-2-propenyl.

7. A method of controlling undesirable grasses in the crop plant wheat which comprises allowing a herbicidally active amount of at least one 5-tetrahydropyranone cyclohexenone oxime ether of the formula I and/or of an agriculturally useful salt of I and/or an ester of I with an acid, as defined in claim 1, to act on the undesirable grasses, their environment or seed.

8. A method of controlling undesirable grasses in the crop plant wheat which comprises allowing a herbicidally active amount of a compound of the formula I as defined in claim 1 wherein $R^1$ is ethyl and $R^2$ is E-3-chloro-2-propenyl or an agriculturally useful salt of the compound to act on the undesirable grasses, their environment or seed.

* * * * *

UNITED STATES PATENT AND TRADEMARK OFFICE
CERTIFICATE OF CORRECTION

PATENT NO.: 5,677,263

DATED: October 14, 1997

INVENTOR(S): RHEINHEIMER et al.

It is certified that error appears in the above-identified patent and that said Letters Patent is hereby corrected as shown below:

On the cover page, in the title, item [54], "S-TETRAHYDROPYRANONE CYCLOHEXENONE OXIME ETHERS AND THEIR USE AS HERBICIDES" should be:
--5-TETRAHYDROPYRANONE CYCLOHEXENONE OXIME ETHERS AND THEIR USE AS HERBICIDES--.

Signed and Sealed this

Ninth Day of December, 1997

Attest:

BRUCE LEHMAN

Attesting Officer

Commissioner of Patents and Trademarks